United States Patent [19]

Franczyk

[11] Patent Number: 5,292,936
[45] Date of Patent: Mar. 8, 1994

[54] PROCESS TO PREPARE AMINO CARBOXYLIC ACID SALTS

[75] Inventor: Thaddeus S. Franczyk, Maryland Heights, Mo.

[73] Assignee: Monsanto Company, St. Louis, Mo.

[21] Appl. No.: 44,682

[22] Filed: Apr. 12, 1993

[51] Int. Cl.⁵ ............... C07C 51/00; C07C 51/097
[52] U.S. Cl. ........................... 562/526; 562/539; 562/553; 562/572
[58] Field of Search ............. 562/526, 539, 553, 571, 562/572

[56] References Cited

U.S. PATENT DOCUMENTS

| | | | |
|---|---|---|---|
| 3,997,478 | 12/1976 | Petro | 252/470 |
| 4,782,183 | 11/1988 | Goto et al. | 562/526 |
| 4,810,426 | 3/1989 | Fields et al. | 260/502.5 |
| 5,220,055 | 6/1993 | Urano et al. | 562/526 X |
| 5,225,592 | 7/1993 | Gomez et al. | 562/526 |

FOREIGN PATENT DOCUMENTS

WO92/06069 10/1991 World Int. Prop. O.

OTHER PUBLICATIONS

Laine et al. "Structure and Activity of Chromium-Promoted Raney Copper Catalysts for Carbon Monoxide Oxidation", Applied Catalysis, 44 (1988) pp. 11–22.

*Primary Examiner*—Arthur C. Prescott
*Attorney, Agent, or Firm*—Frank D. Shearin

[57] ABSTRACT

An improved process is disclosed to prepare an amino carboxylic acid salt. According to the process, an aqueous solution of an amino alcohol is contacted with an alkali metal hydroxide in the presence of an effective amount of a Raney copper catalyst that has from about 50 parts per million to about 10,000 parts per million of an element selected from the group consisting of chromium, titanium, niobium, tantalum, zirconium, vanadium, molybdenum, manganese, tungsten, cobalt, nickel and mixtures thereof.

10 Claims, No Drawings

PROCESS TO PREPARE AMINO CARBOXYLIC ACID SALTS

BACKGROUND OF THE INVENTION

This invention relates to the preparation of amino carboxylic acid salts, and more particularly, relates to a method for the preparation of amino carboxylic acid salts by the reaction of amino alcohols with an alkali metal hydroxide in the presence of a Raney copper catalyst.

Amino carboxylic acid salts are useful in various applications. The glycine salt, for example, can be neutralized to glycine, which is widely used as an additive in processed meat, beverages, and in other processed food stuffs. It is also used widely as a raw material for pharmaceuticals, agricultural chemicals and pesticides. Iminodiacetic acid salt can be neutralized to iminodiacetic acid, and is used in various applications such as a raw material for the preparation of agricultural chemicals and pharmaceuticals. Nitrilotriacetic acid salt can be converted into nitrilotriacetic acid which is useful as a detergent builder. Other amino carboxylic acids that can be prepared by the process of the present invention have useful applications.

U.S. Pat. No. 4,782,183 to Goto et al. discloses a method for the manufacture of amino carboxylic acid salts which comprises subjecting an amino alcohol to an alkali metal hydroxide in the presence of a Raney copper catalyst.

In a patent application published by WIPO as WO 92/06069 on Apr. 16, 1992, a process is disclosed for producing glycine, iminodiacetic acid and nitrilotriacetic acid salts by contacting monoethanolamine, diethanolamine or triethanolamine with an alkali metal hydroxide in the presence of a Raney copper catalyst, wherein at least some of the Raney copper catalyst has been rejuvenated by treating the catalyst under reflux conditions with formic acid (attorney docket No 39-21(3145)).

A journal article "Structure and Activity of Chromium-Promoted Raney Copper Catalyst for Carbon Monoxide Oxidation" by Laine et al., *Applied Catalysis*, 44 (1-2), pages 11-22, discloses that chromium-promoted Raney copper catalysts were prepared, and their activity for the oxidation of carbon monoxide was measured. The surface area of the Raney copper catalyst was directly related to the aluminum content in the precursor alloy and to a lesser extent to the presence of chromium. Bulk cuprous oxide and cupric oxide were detected by X-ray diffraction in the Raney copper catalyst. The presence of chromium inhibited the formation of cupric oxide but not of cuprous oxide. The activity decreased as chromium content increased.

U.S. Pat. No. 4,810,426 to Fields et al., discloses a process for the production of N-phosphonomethylglycine by oxidizing N-phosphonomethylethanolamine or the cyclic internal ester thereof with an excess of an aqueous alkali and a copper catalyst, and thereafter heating at a temperature between 200° and 300° C. Thereafter, the salt is neutralized with an acid to produce the desired N-phosphonomethylglycine.

Although satisfactory results are achieved by the processes of the prior art to convert an amino alcohol to a amino acid using a copper catalyst, or even a Raney copper catalyst, it has been found that upon repeated usage of the Raney copper catalyst, the catalyst tends to agglomerate, and the activity of the catalyst decreases. Now, it has been found, in accordance with the teachings of the present invention, that the activity of the Raney copper catalyst can be extended to a significant degree, permitting more economic utilization of the catalyst.

SUMMARY OF THE INVENTION

These and other advantages are achieved in a process to manufacture an amino carboxylic acid salt which comprises contacting an aqueous solution of an amino alcohol represented by the formula:

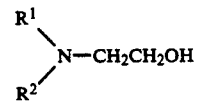

wherein $R^1$ and $R^2$ are individually selected from the group consisting of hydrogen, $-CH_2CH_2OH$, $-CH_2COOH$, an alkyl group having from 1 to 6 carbon atoms, and phosphonomethyl; with an alkali metal hydroxide in the presence of an effective amount of a Raney copper catalyst containing from about 50 parts per million to about 10,000 parts per million of an element selected from the group consisting of chromium, titanium, niobium, tantalum, zirconium, vanadium, molybdenum, manganese, tungsten, cobalt, nickel and mixtures thereof.

DETAILED DESCRIPTION OF THE INVENTION

The amino alcohols which are useful as starting materials in the process of the present invention are known to those skilled in the art. When $R^1$ and $R^2$ are both hydrogen, the amino alcohol is monoethanolamine. When one of $R^1$ and $R^2$ is $-CH_2CH_2OH$ or $-CH_2COOH$, and the other R group is hydrogen, the amino alcohol is diethanolamine. When both $R^1$ and $R^2$ are $-CH_2CH_2OH$ or $-CH_2COOH$, the amino alcohol is triethanolamine. The resulting amino carboxylic acid salts from these starting amino alcohols would be the salts of glycine, iminodiacetic acid and nitrilotriacetic acid, respectively.

In the above formula, $R^1$ and/or $R^2$ can also be an alkyl group having from 1 to 6 carbon atoms, for example, methyl, ethyl, propyl, isopropyl, butyl, isobutyl and the like. There would then be provided corresponding amino acids with these alkyl groups which would be useful in a number of applications. $R^1$ or $R^2$ can also be a phosphonomethyl group such that the starting amino acid would be N-phosphonomethylethanolamine, and the resulting amino acid would be N-phosphonomethylglycine. If one of $R^1$ or $R^2$ were phosphonomethyl, and the other were $-CH_2CH_2OH$, the resulting amino acid would be N-phosphonomethyliminodiacetic acid, which can be converted to N-phosphonomethylglycine by any number of techniques known to those skilled in the art. If one of $R^1$ or $R^2$ were phosphonomethyl, and the other were an alkyl group, the resulting amino acid would be an N-alkyl-N-phosphonomethylglycine which could be converted to N-phosphonomethylglycine by the teachings in U.S. Pat. No. 5,068,404 to Miller and Balthazor.

Raney copper catalysts can be prepared by techniques known to those skilled in the art from alloys containing copper and aluminum, and thereafter, the aluminum is leached from the alloy with an aqueous alkali metal hydroxide to provide an activated Raney copper. The activated Raney copper can then be treated with a nitrate, sulfate or other salt of an element selected from the group consisting of chromium, titanium, niobium, tantalum, zirconium, vanadium, molybdenum, manganese, tungsten, cobalt, nickel and mixtures thereof, but it is preferred to incorporate the above elements into the copper aluminum alloy during the preparation of the Raney copper. Of the above elements, chromium, molybdenum, and mixtures of chromium and molybdenum are preferred.

The amount of added element in the Raney copper can vary within wide limits. Improved results for the conversion of an amino alcohol to an amino acid can be seen with as little as 50 parts per million added element in the copper. As an upper limit, the Raney copper can contain up to about 10,000 parts per million added element, and the Raney copper can even contain higher levels, although such higher levels do not provide significantly improved results for the conversion of the amino alcohol to the corresponding amino acid. It is preferred to use a Raney copper catalyst having a content of added element between about 50 and 5000 parts per million.

The amount of catalyst to be used to convert the amino alcohol to the corresponding amino acid can range between about 1% and about 70% by weight, preferably 10 to 40% by weight based on the amount of the starting amino alcohol. The catalyst can generally be used repeatedly in the reaction for a greater number of times than a Raney copper catalyst without the added element.

The alkali metal hydroxides for use in the process of the present invention include lithium hydroxide, sodium hydroxide, potassium hydroxide, rubidium hydroxide and cesium hydroxide. The amount of the hydroxide of the alkali metal to be used is an equivalent amount in the range of 1.0 to 2.0 equivalents relative to the hydroxyl group of the amino alcohols to be used in the reaction. The hydroxide can be in the form of flakes, powder, pellets or an aqueous solution. Because of their ready availability and ease of handling, sodium hydroxide and potassium hydroxide are preferred, and sodium hydroxide is especially preferred.

In the process of the present invention, it is only necessary to contact the amino alcohol with an alkali metal hydroxide in the presence of the Raney copper catalyst containing about 100 parts per million to about 10,000 parts per million of the added element at a temperature between about 120° C. and 220° C., preferably between about 140° C. and about 200° C. At temperatures above about 220° C., the Raney copper catalyst begins to lose selectivity. At temperatures below about 120° C., satisfactory results can be obtained, but the reaction is slow.

Pressure is required for the reaction to proceed at the temperatures indicated above. However, the reaction pressure is desired to be as low as possible to insure high reaction velocity. Generally, it is necessary to exceed the minimum pressure at which the reaction proceeds in the liquid phase, preferably between 5 and about 30 kg/cm$^2$, preferably in the range of 5 to 20 kg/cm$^2$. The conversion of the amino alcohol to the corresponding salt of the amino acid proceeds with the liberation of hydrogen, which should be vented with care from the reaction vessel.

The invention is further illustrated by, but not limited to, the following examples:

EXAMPLE 1

This example illustrates the results that are obtained using a Raney copper catalyst without chromium.

Into a 300 ml nickel autoclave equipped with a stirrer was charged diethanolamine (62.5 g, 0.59 mol.) water (60 ml) and a 50% aqueous solution of sodium hydroxide (50 g NaOH, 1.25 mol.) Then, a Raney copper catalyst (12.4 g) was added to the autoclave. The autoclave was sealed, and heated to a temperature of 160° C. under a pressure of 9.5 Kg/cm$^2$ while stirring the liquid phase in the autoclave. Heating was continued until hydrogen gas was no longer evolved, indicating that the reaction was complete. The reaction time was recorded, and the catalyst was reused in a subsequent run. In all cases the yield of iminodiacetic acid was about 95%. The results are shown in Table 1.

TABLE 1

| Cycle | Reaction Times for Repeated Use of the Same Raney Cooper Catalyst Reaction Time (hours) |
|---|---|
| 1 | 4.0 |
| 2 | 5.2 |
| 3 | 4.8 |
| 4 | 5.2 |
| 5 | 5.9 |
| 6 | 6.5 |
| 7 | 7.0 |
| 8 | 7.2 |
| 9 | 8.0 |

EXAMPLE 2

This example illustrates the use of a Raney copper catalyst containing chromium according to the present invention.

The procedure of Example 1 was repeated except that a Raney copper catalyst containing 943 parts per million chromium was used in 25 cycles of the catalyst. The results are shown in Table 2.

TABLE 2

| Cycle | Reaction Times for Repeated Use of a Chromium Promoted Raney Cooper Catalyst Reaction Time (hours) |
|---|---|
| 1 | 5.8 |
| 2 | 6.7 |
| 3 | 6.6 |
| 4 | 6.2 |
| 5 | 6.4 |
| 6 | 6.3 |
| 7 | 6.0 |
| 8 | 6.0 |
| 9 | 6.0 |
| 10 | 6.2 |
| 15 | 7.0 |
| 20 | 7.0 |
| 25 | 8.0 |

A comparison of the data in Table 1 and Table 2 shows that the reaction times for the Raney copper catalyst containing chromium is longer for about the first five cycles, but remains relatively steady for an additional 20 cycles. The reaction time at cycle 25 is 8 hours, whereas a reaction of 8 hours was reached after only 9 cycles using a standard Raney copper catalyst (Table 1).

EXAMPLE 3

This example illustrates the use of a Raney copper catalyst treated with chromic nitrate prior to its first use to convert diethanolamine to the disodium salt of iminodiacetic acid according to the present invention.

Into a 50 ml beaker is placed activated Raney copper (4.13 g), water (10 ml) and chromic nitrate (0.50 g of 15 weight % $Cr(NO_3)_3$, 4,000 ppm Cr based on the total mass of copper), and the mixture is allowed to stand 15 minutes. The Raney copper and the supernatant are transferred to a 160 ml nickel autoclave along with diethanolamine (21.2 g, 0.20 mol.) water (10 ml) and a 50% aqueous solution of sodium hydroxide (19 g NaOH, 0.42 mol.). The autoclave is sealed, and heated to 160° C. under 9.5 $Kg/cm^2$ pressure while stirring the liquid phase in the autoclave. Heating is continued until hydrogen gas is no longer evolved, indicating that the reaction is complete. The reaction time is recorded and the catalyst is reused without further addition of chromium. The results are shown in Table 3.

TABLE 3

Reaction Times for Raney Cooper Catalyst Prepared by Adding Chromium Nitrate

| Cycle | Reaction Time (hours) |
|---|---|
| 1 | 4.0 |
| 2 | 3.5 |
| 3 | 3.5 |
| 4 | 3.1 |
| 5 | 2.7 |
| 6 | 2.7 |
| 7 | 2.7 |
| 8 | 2.7 |
| 9 | 2.7 |
| 10 | 2.7 |
| 11 | 3.0 |
| 12 | 2.8 |
| 13 | 3.1 |
| 14 | 3.1 |
| 15 | 3.2 |

As the data in Table 3 indicates, reaction times improve over the first 4 cycles, and then remains relatively constant, ranging from 2.7 to 3.2 hours for the remaining cycles. Using untreated Raney copper as the catalyst, only the first cycle falls within a 2.7–3.1 hour reaction time, and subsequent cycles require progressively longer periods (eg., 3.5 to 7 hours) to reach endpoint.

EXAMPLE 4

This example illustrates the use of the Raney copper catalyst containing chromium to convert N-2-(hydroxyethyl)aminomethylphosphonic acid to N-phosphonomethylglycine.

Into a 160 ml nickel autoclave equipped with a stirrer is charged N-2-(hydroxyethyl)aminomethylphosphonic acid (16.84 g, 0.11 mol.) water (11.3 ml) and 45 weight % potassium hydroxide (48.7 g, 0.39 mol.) and Raney copper catalyst containing 943 parts per million chromium (3.53 g). The autoclave is sealed and heated to 160° C. under a pressure of 9.5 $Kg/cm^2$ while stirring the liquid phase in the autoclave. After 1.85 hours, hydrogen evolution ceases. The yield of N-phosphonomethylglycine as its potassium salt is 98.5%.

EXAMPLE 5

This example illustrates the conversion of N-phosphonomethyl-2-oxazolidone to N-phosphonomethylglycine using a Raney copper catalyst containing chromium.

The procedure of Example 4 is repeated except that N-phosphonomethyl-2-oxazolidone made by the process described in U.S. Pat. No. 4,547,324 is used instead of N-2(hydroxyethyl)aminomethylphosphonic acid. After 2 hours of heating, the yield of N-phosphonomethylglycine is 86.2% as determined by HPLC analysis.

EXAMPLE 6

This example illustrates the conversion of diethanolamine to disodium iminodiacetate using a Raney copper catalyst containing molybdenum.

The procedure of Example 1 was repeated except that a Raney copper catalyst containing about 500 parts per million molybdenum was used in 12 cycles of the catalyst. After each cycle 2.5 percent of the Raney copper was replaced with fresh catalyst. The results are shown in Table 4.

TABLE 4

Reaction Times for Raney Cooper Catalyst with Added Molybdenum

| Cycle | Reaction Time (hours) |
|---|---|
| 1 | 3.1 |
| 2 | 3.6 |
| 3 | 3.5 |
| 4 | 3.9 |
| 5 | 4.2 |
| 6 | 4.5 |
| 7 | 4.7 |
| 8 | 4.9 |
| 9 | 5.0 |
| 10 | 5.2 |
| 11 | 5.4 |
| 12 | 5.5 |

As can be seen by comparing the reaction times in Table 4 with the reaction times in Table 1, the Raney copper containing molybdenum provided faster reactions than Raney copper without the added molybdenum. In addition, there was no adverse effect on selectivity, i.e., no increased levels of unwanted byproducts.

EXAMPLE 7

The procedure of Example 6 is repeated except that the Raney copper contains about 500 ppm chromium and 500 ppm molybdenum. Substantially the same results are obtained.

EXAMPLE 8

The procedure of Example 2 is repeated in a series of tests using Raney copper containing titanium, zirconium, niobium, tantalum, vanadium, manganese, tungsten, cobalt or nickel. In each of these tests the results are not as good as the results obtained in Example 2, but are better than the results obtained in Example 1.

Although the invention has been described in terms of specified embodiments which are set forth in considerable detail, it should be understood that this is by illustration only, since alternative embodiments and operating techniques will become apparent to those skilled in the art in view of the disclosure. For example, any number of carboxylic acids other than those described herein can be prepared by the conversion of the corresponding amino alcohol using the Raney copper catalyst containing an added element in accordance with the teachings of the present invention. Accordingly, modifications can be made without departing from the spirit of the described invention.

What is claimed is:

1. A process to manufacture an amino carboxylic acid salt which comprises contacting an aqueous solution of an amino alcohol represented by the formula:

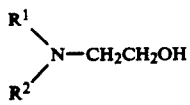

wherein $R^1$ and $R^2$ are individually selected from the group consisting of hydrogen, $-CH_2CH_2OH$, $-CH_2COOH$, an alkyl group having from 1 to 6 carbon atoms, and phosphonomethyl; with an alkali metal hydroxide in the presence of an effective amount of a Raney copper catalyst containing from about 50 parts per million to about 10,000 parts per million of an element selected from the group consisting of chromium, titanium, niobium, tantalum, zirconium, vanadium, molybdenum, manganese, tungsten, cobalt, nickel and mixtures thereof.

2. A process of claim 1 wherein the temperature to convert the amino alcohol to the amino acid salt is between about 120° C. and about 220° C.

3. A process of claim 1 wherein the Raney copper catalyst contains from about 50 parts per million to about 5000 parts per million chromium.

4. A process of claim 1 wherein the Raney copper catalyst contains from about 50 parts per million to about 5,000 parts per million molybdenum.

5. A process of claim 1 wherein the Raney copper catalyst contains from about 50 parts per million to about 5,000 parts per million chromium and from about 50 parts per million to about 5,000 parts per million molybdenum.

6. A process of claim 1 wherein the amino alcohol is diethanolamine.

7. A process of claim 1 wherein $R^1$ is phosphonomethyl and $R^2$ is hydrogen.

8. A process of claim 1 wherein the alkali metal hydroxide is sodium hydroxide or potassium hydroxide.

9. A process of claim 1 wherein the amount of catalyst is between about 1 and 70% by weight, based on the amount of amino alcohol.

10. A process of claim 9 wherein the amount of catalyst is between about 10 and about 40% by weight.